(12) United States Patent
Helfenbein

(10) Patent No.: US 7,575,432 B2
(45) Date of Patent: Aug. 18, 2009

(54) TORQUE TRANSMISSION FOR A SURGICAL OR DENTAL ROTATING TOOL

(75) Inventor: Gerald Helfenbein, Gilgenberg (AT)

(73) Assignee: W & H Dentalwerk Bürmoos GmbH, Bürmoos (AT)

( * ) Notice: Subject to any disclaimer, the term of this patent is extended or adjusted under 35 U.S.C. 154(b) by 70 days.

(21) Appl. No.: 10/481,549

(22) PCT Filed: Apr. 18, 2003

(86) PCT No.: PCT/AT03/00115

§ 371 (c)(1),
(2), (4) Date: Apr. 19, 2004

(87) PCT Pub. No.: WO03/086222

PCT Pub. Date: Oct. 23, 2003

(65) Prior Publication Data

US 2004/0161723 A1 Aug. 19, 2004

(30) Foreign Application Priority Data

Apr. 18, 2002 (AT) .............................. A 603/2002

(51) Int. Cl.
*A61C 3/00* (2006.01)
*A61C 3/02* (2006.01)
(52) U.S. Cl. ................. 433/114; 433/84; 433/126; 433/165
(58) Field of Classification Search .............. 433/84, 433/85, 114–115, 125, 127, 131–134, 165–166, 433/126
See application file for complete search history.

(56) References Cited

U.S. PATENT DOCUMENTS

| 3,727,313 | A | * | 4/1973 | Graham | 433/125 |
| 3,762,052 | A | * | 10/1973 | Melde | 433/120 |
| 4,014,099 | A | | 3/1977 | Bailey | 433/128 |
| 4,564,354 | A | * | 1/1986 | Rosenstatter | 433/133 |
| 5,000,684 | A | * | 3/1991 | Odrich | 433/125 |
| 5,022,857 | A | * | 6/1991 | Matsutani et al. | 433/85 |
| 5,069,620 | A | * | 12/1991 | Matsutani et al. | 433/82 |

(Continued)

FOREIGN PATENT DOCUMENTS

DE 2905484 8/1979

(Continued)

*Primary Examiner*—John J Wilson
(74) *Attorney, Agent, or Firm*—Friedrich Kueffner

(57) ABSTRACT

The invention concerns a handpiece for a surgical or dental tool (3), which can be inserted in the head of the handpiece (1) through an insertion hole (14) into a tool holder (2) and is rotationally supported by means of two axially separated bearings (12, 13), with positive torque transmission (8) to the tool (3) by the drive (9) installed in the handpiece, such that the tool possibly has a longitudinal bore (6) for supplying cooling liquid to the work site, and the handpiece (1) possibly has a short, fixed feed tube (7), which extends into the longitudinal bore and is sealed from the tool (3).

To increase the torque that can be transmitted, the invention is characterized by the fact that the torque transmission (8) occurs in the region of the bearing (13) that is adjacent to the insertion hole (14).

The invention also concerns the development of suitable tools.

14 Claims, 1 Drawing Sheet

U.S. PATENT DOCUMENTS

| | | | | |
|---|---|---|---|---|
| 5,096,421 A | * | 3/1992 | Seney | 433/82 |
| 5,816,803 A | * | 10/1998 | Nakanishi | 433/82 |
| 6,068,632 A | * | 5/2000 | Carchidi et al. | 606/79 |

FOREIGN PATENT DOCUMENTS

| DE | 3040537 | 5/1982 |
|---|---|---|
| DE | 199 18 638 A1 | 11/2000 |
| EP | 0470324 | 2/1992 |
| EP | 0642770 | 3/1995 |
| WO | 8301099 | 3/1983 |
| WO | WO 9412117 A1 * | 6/1994 |

* cited by examiner

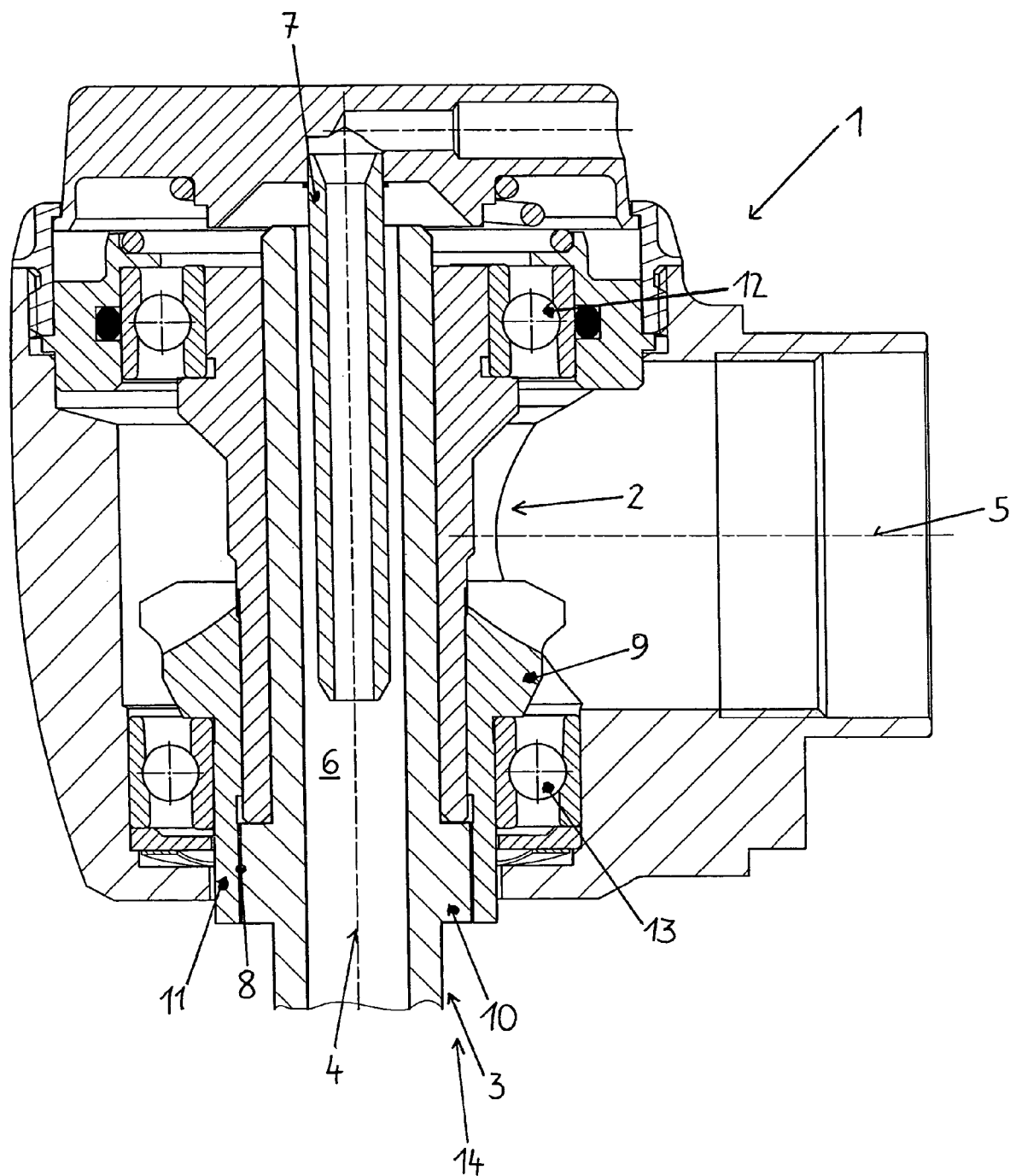

TORQUE TRANSMISSION FOR A SURGICAL OR DENTAL ROTATING TOOL

The invention concerns a surgical or dental tool, which can be inserted in the head of a handpiece through an insertion hole into a tool holder and is rotationally supported by means of two axially separated bearings, with positive torque transmission to the tool, which possibly has a longitudinal bore for supplying cooling liquid to the work site, and the handpiece possibly has a short, fixed feed tube, which extends into the longitudinal bore and is sealed from the tool, such that the torque transmission occurs in the region of the bearing that is adjacent to the insertion hole.

A handpiece that does not conform to this general type of handpiece, which does not have a small feed tube and thus has no possibility of internal supply of coolant or rinsing agent through the tool, and which has a different type of torque transmission, is described in AT 375 011 B, in which, with the tool nondetachably connected, a gear, a bearing for the tool, and a part of the head housing are provided as an inserted part. The reason for these measures is the desire to achieve the greatest possible miniaturization of the head of the handpiece. For this reason, a tool holder is abandoned, and the high cost of the inserted part is accepted instead. It is obvious that this inserted part, which is precisely adapted to the rest of the head (and the second bearing!), is extremely expensive compared to the tool and, due to the bearing, extremely difficult to clean and to disinfect.

Another handpiece without a small feed tube, which also does not conform to this general type of handpiece, is described in U.S. Pat. No. 5,542,846 A. In this case, torque is transmitted via a type of retaining ring. In this regard, the retaining ring is held in a guide sleeve in such a way that it cannot rotate, and it is tilted by a spring, so that it simultaneously turns the shaft of the tool by frictional engagement.

In the fields of surgery and dental medicine, tools have long been inserted in the tool holders of handpieces, so that the intended rotary, oscillating, or vibrating motion is transmitted to the tool by the tool holder. For this purpose, there are many different systems and many specially designed tool shafts that are adapted to the given tool holders. Especially for use in the surgical field, in which in many cases larger volumes of bone or other hard materials must be removed than in the dental field, it is important to use drills or tools in general, which have a built-in supply line for a coolant. This serves the purpose of efficient cooling of the work site and orderly removal of the material that has been cut from the machining site.

Furthermore, the same handpieces and thus the same tool holders are also used to cut threads in holes drilled into the bone and to screw implants into the threads produced in this way. Especially during the screwing in of the implants, torques are transmitted, which are significantly higher than during the drilling of the hole in the bone or tooth. Roughly speaking, it can be said that torques of up to 80 newton—centimeters are applied here, which must then be transmitted by a tool shaft with a typical nominal diameter of 2.35 mm. In this connection, it must also be considered that these tool shafts have a longitudinal hole on the inside to be able to hold the feed tube of the tool holder, through which the cooling liquid is supplied, so that only a thin outer wall of the tool shaft is actually available for transmitting the torque.

The tool holders mainly being used today, which correspond to the state of the art specified at the beginning, transmit the torque in the following way: The tool shaft is flattened at its upper end over a height of several millimeters, and this flattening abuts a correspondingly protruding, flat part of the tool holder and thus forms a positive-locking connection with the tool holder. In this region of the tool shaft, its wall thickness is extremely diminished, since, as viewed axially, an annular groove, which axially secures the tool in the tool holder, is located just below this flattening.

As a result, the available lever arm, with which the torque is transmitted, becomes extremely small, so that, during the cutting of threads and especially during the screwing in of implants, it often happens that the tool is plastically deformed in this region and can no longer be removed from the tool holder.

Another very significant disadvantage of the state of the art is that a seal can be produced only with extreme difficulty between the rotating drill and the small feed tube of the tool holder that extends coaxially with the drill axis into the interior of the longitudinal hole. The solutions to this problem that are presently in use are such that this stationary feed tube extends far out of the handpiece (and is thus at extreme risk of being damaged), that the tool shaft has a bulge in a region close to the lower end of the feed tube (approximately in the middle of the length of the tool!!!), that a bore through this bulge is created normal to the tool axis, that, during the production of the tool, a core, which simulates the small feed tube, is inserted in the longitudinal bore of the tool, that a sealing material (silicone) or the like is then injected through the transverse bore, and that, during solidification of this sealing material, the inserted core is moved to prevent it from bonding with the sealing material.

After solidification or curing has occurred, the core is removed, and the injected sealing compound forms a completely irregularly shaped seal on about half the length of the tool.

From everything that has been said, it is clear that the creation of a tool and its holder, which satisfy requirements during use without any problems, is urgently needed, and that not only should this new tool holder and the new tool satisfy the requirements during use, but also the production costs should be reduced, so that it is possible to satisfy another demand of surgeons and dentists, namely, that tools of this type should be disposable after a single use, which is desirable for reasons of hygiene, but presently is not possible for reasons of cost. In this regard, it must also be considered that especially the cutting parts of the tool have depressions, recesses, cavities, and the like, which, during invasive procedures performed with them, readily pick up organic material from the patient being treated, which can then be removed only with extreme difficulty.

The invention achieves the stated objectives by providing that the torque is positively transmitted in the tool-side region of the tool holder, preferably by a polygon and more preferably by a regular hexagon, and that the seal that is possibly to be produced between the small feed tube of the tool holder and the longitudinal bore of the tool is produced by a seal in the uppermost region of the tool.

In this way, any reduction in the cross section of the tool in the axial region that is acted on by the torque, which, of necessity, is already very small, is reliably avoided, while at the same time, the space for the seal in tools which have internal cooling is moved to a point at which a seal of this type can be easily and reliably inserted, i.e., the upper end region of the tool shaft.

Tools that do not have internal cooling, for example, the tools for screwing in implants that were mentioned at the beginning, can already be fully installed in the region in which the torque is transmitted from the tool holder and require only a recess in their upper, practically torque-free region to be able to hold the small feed tube.

In accordance with the invention, therefore, the tool holder is designed in such a way that the torque is positively transmitted in its uppermost, tool-side region, and that the small feed tube for the cooling liquid ends, as viewed axially, above the torque transmission to the tool.

A refinement of the invention provides that the element for the positive transmission of the torque in the tool holder is formed as a single piece with the gear that transmits the torque from the drive. In this way, it is possible to avoid the torsion between this gear and the actual tool holder that repeatedly occurs in the state of the art.

The invention is explained in greater detail below with reference to the drawing in the sole FIGURE.

The sole drawing shows the front end of a handpiece 1 in a cross section along the axis of rotation 4 of the tool 3 and the axis of rotation 5 of the drive (not shown) in the handpiece 1.

The tool 3, which in the case shown here is a drill, milling cutter, or the like, with internal cooling has a longitudinal bore 6 for supplying cooling liquid. The longitudinal bore 6 runs from the upper end of the shaft to the actual work area (not shown), where the cooling liquid passes through the tool head to the actual working site through suitable channels. To introduce the cooling liquid into the longitudinal bore 6 of the tool 3, a small feed tube 7 is provided in the tool holder 2. It runs coaxially with the tool 3, and its dimensions are chosen in such a way that its outside diameter is smaller than the inside diameter of the longitudinal bore 6, and that, viewed axially, it ends in a region of the tool holder 2 that is still above the region 8 of torque transmission.

This region 8 of torque transmission is located in the lowermost section of the head of the handpiece. In the application and the claims, the terms "below" and "above" are understood to mean these directions as shown in the drawing. In the tool holder, "below" is the side from which the tool is inserted; for the tool, "below" is the side on which the tool head is located, and "above" is the side of the tool shaft into which the small feed tube 7 is inserted.

The torque transmission occurs, on the one hand, by means of a sleeve-like extension 11 of the drive gear 9, which (extension 11) extends as far as this region, and, on the other hand, the shaft of the tool 3 has a bulge 10, with the proviso that the inner contour of the sleeve-like extension 11 corresponds to the outer contour of the bulge 10 and that, as a result of this correspondence, positive-locking prevention of torsion is created.

As is readily apparent from what has been said, and as is immediately obvious from the drawing, the torque is transmitted from the gear 9 via its sleeve-like extension 11 and the positive-locking connection with the bulge 10 to the shaft of the tool 3, which experiences no weakening whatsoever from this axial region towards the bottom to the machining head (not shown).

If, instead of the tool 3 with internal cooling shown in the drawing, a key or transmission pin or the like is inserted, with which, for example, an implant is screwed in, then, as is readily apparent, this can be fully formed immediately below the region in which the small feed tube 7 ends, i.e., the whole cross section is available for the entire region that is being acted upon with the high torque for the job of screwing it in. Under certain circumstances, this cross section may also be larger than that of the tool 3 shown in the drawing, since, as the drawing shows, starting from the region of torque transmission, the tool head 1 and the tool holder 2 make it possible to use a tool shaft with a larger diameter (in this region, but, of course, not in the upper region of the tool holder).

If the use of drills with the aforementioned standard diameter of 2.35 mm is abandoned and a change is made, for example, to 3 mm, then the longitudinal bore for supplying cooling liquid can be created by machining, and one is no longer dependent on the extremely expensive method of sink erosion. The number of possible applications for drills of this type is greatly increased due to the cost reduction that can be achieved in this way.

The details of the design, such as the materials that can be used, the production methods, and adaptation to existing systems, can be easily determined by an expert familiar with the invention and do not need to be discussed here.

In another embodiment the tool has a seal that extends radially inwardly at or near its handpiece end. The tool can also have a solid cross section in its axial region between the torque transmission and its end remote from the handpiece.

The invention claimed is:

1. A handpiece in combination with a surgical or dental tool, the tool having a tool end, a handpiece end and a shaft extending between the tool end and the handpiece end, wherein the shaft comprises a first shaft section and a region for positive torque transmission, which is located a distance from the handpiece end of the tool and which comprises a polygonal cross section, wherein the polygonal cross section is larger than a cross section of the first shaft section of the tool, the handpiece having a head with an insertion hole and a tool holder mounted in the head of the handpiece, wherein the handpiece end of the tool is adapted to be inserted in the head of the handpiece through an insertion hole into the tool holder, wherein the tool holder is rotationally supported by means of two axially separated bearings mounted in the head of the handpiece, with positive torque transmission to the tool, wherein the torque transmission occurs in the region of the bearing that is adjacent to the insertion hole, and wherein the torque transmission comprises a polygonal recess in the tool holder, wherein the tool holder is elongate and comprises a first section for accommodation of at least a part of the first shaft section of the tool, the first section of the tool holder having a first internal diameter, wherein the tool holder comprises a second section for accommodation of the region for positive torque transmission of the tool, the second section of the tool holder having a second internal diameter, and wherein the second internal diameter is larger than the first internal diameter.

2. The combination in accordance with claim 1, wherein the torque transmission occurs in the region of the insertion hole.

3. The combination in accordance with claim 2, wherein the torque transmission occurs in the region of the insertion hole away from the two bearings.

4. The combination in accordance with claim 1, wherein the polygonal recess of the torque transmission is a regular hexagon.

5. The combination in accordance with claim 1, wherein the polygonal cross section has the shape of a regular hexagon.

6. The combination in accordance with claim 1, the shaft has a solid cross section in its axial region between the torque transmission region and the tool end remote from the handpiece end.

7. The combination in accordance with claim 1, wherein the tool has a longitudinal bore for supplying cooling liquid to the work site.

8. The combination in accordance with claim 7, wherein the handpiece has a short, fixed feed tube, which extends into the longitudinal bore and is sealed from the tool.

9. The combination in accordance with claim 8, wherein the feed tube ends in an axial region before the torque transmission.

10. The combination in accordance with claim 8, wherein the feed tube ends in an axial region between the two bearings.

11. The combination in accordance with claim 1, wherein the torque transmission is formed by the insertion hole of the tool holder.

12. The combination in accordance with claim 1, wherein the tool holder includes a drive member having a sleeve-like extension in which the polygonal recess is formed.

13. The combination in accordance with claim 12, wherein the sleeve-like extension is arranged to co-operate with the bearing adjacent the insertion hole.

14. The combination in accordance with claim 1, wherein the polygonal cross section of the region for positive torque transmission of the tool has a width which is substantially equal to the outer diameter of an adjacent part of the first section of the tool holder for accommodation of the least a part of the first shaft section of the tool.

* * * * *